United States Patent [19]

Beneš et al.

[11] 4,077,963
[45] Mar. 7, 1978

[54] QUATERNARY SALTS OF METHACRYLIC OR ACRYLIC ESTERS

[75] Inventors: Milan Beneš; Jan Peška, both of Prague, Czechoslovakia

[73] Assignee: Ceskoslovensak akademie Ved, Prague, Czechoslovakia

[21] Appl. No.: 725,150

[22] Filed: Sep. 20, 1976

Related U.S. Application Data

[62] Division of Ser. No. 302,897, Nov. 1, 1972, Pat. No. 4,011,204.

[30] Foreign Application Priority Data

Nov. 2, 1971 Czechoslovakia .................. 7687/71
Nov. 2, 1971 Czechoslovakia .................. 7688/71

[51] Int. Cl.² ........................................ C07D 213/89
[52] U.S. Cl. ........................... 260/290 V; 260/286 Q; 260/302 R; 260/456 A
[58] Field of Search ........ 260/456 A, 286 Q, 294.8 F, 260/302 R, 290 V

[56] References Cited

U.S. PATENT DOCUMENTS 2,677,679  5/1954  Barney ........................... 260/456 A
2,857,310  10/1958  Heininger ........................ 260/286 Q

*Primary Examiner*—Paul M. Coughlan, Jr.

[57] ABSTRACT

The invention relates to quaternary cationic monomers and polymers and copolymers prepared thereof, based upon salts of methacrylic or acrylic esters of the general formula I

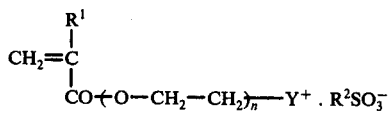

where
$R^1$ is H or $CH_3$
$R^2$ is $CH_3$, $C_6H_5$ or p-$CH_3C_6H_4$
$n$ is 1 or 2
and
$Y^+$ is $-N^+(CH_3)_3$, $-N^+(CH_3)_2CH_2CH_2OH$,

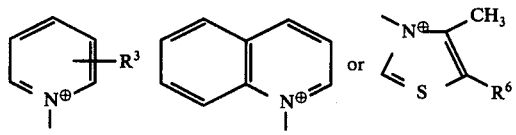

where
$R^3$ is H, $CH_3$, $CONH_2$, CHO, $COCH_3$
and
$R^4$ is H or $CH_2CH_2OH$.

The invention further relates to some methods for preparation of monomers, polymers and copolymers of the aforegiven salts. The polymers and copolymers exhibit the properties of polyelectrolytes and ion exchange resins.

6 Claims, No Drawings

QUATERNARY SALTS OF METHACRYLIC OR ACRYLIC ESTERS

This is a divisional application of Ser. No. 302,897, filed Nov. 1, 1972, U.S. Pat. No. 4,011,204.

STATEMENT OF THE OBJECT OF THE INVENTION

Monomers of the methacrylate type are often used for the preparation of cationic polyelectrolytes. They can be obtained essentially in two ways. Either by alkylation of tertiary aminoalkyl methacrylates by an alkylation agent or by alkylation of tertiary amines by an alkylating methacrylate.

Among the analogous compounds, methacrylic ester of 2-hydroxyethyltrimethylammonium methylsulfate,

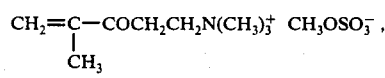

which is produced by methylation of 2-dimethylamino-ethyl methacrylate (Brit. Pat. No. 784,051 and U.S. Pat. Nos. 2,677,679 and 2,824,861), obtained a wide technological use. Further, the preparation of methacrylic ester of 1-(2-hydroxyethyl)pyridinium chloride by the reaction of 2-chloroethyl methacrylate with pyridine was described (Brit. Pat. No. 784,051).

According to the invention, monomeric quaternary salts of methacrylic or acrylic esters of the general formula II

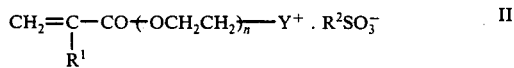

are prepared by the reaction of sulfoester of the general formula III

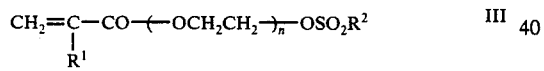

with the corresponding tertiary amine. The meaning of substituents $R^1$, $R^2$ and $Y^+$ and of the symbol $n$ in the formulas II and III are the same as in the aforementioned formula I.

This reaction can be advantageously carried out in the presence of polymerization inhibitors, without solvent or in an inert solvent at ambient or elevated temperature. The product may by purified, for instance, by dissolving in water and extraction of unreacted components by a suitable solvent.

An advantage of the presented method is employment of the large alkylation power of sulfoester group. The reaction proceeds under mild conditions and reaches high yield. It is possible to prepare products derived from less reactive tertiary bases, which require in the preparation from chloro derivatives long reaction periods and high temperature, i.e., the conditions when the thermically induced polymerization interferes even in the presence of an inhibitor. Another advantage is that sulfoester III can be prepared from a hydroxy derivative (e.g., 2-hydroxyethyl methacrylate) which contains various amounts of a divinylic component (ethylene dimethacrylate). The latter compound remains unchanged in the reaction mixture and is advantageously removed together with an inhibitor and any unreacted starting material by extraction of the aqueous solution. This extracted solution can be then advantageously directly used for polymerization.

The employment of much more reactive sulfoesters of hydroxyalkyl methacrylates enables to prepare quaternary methacrylates derived from low reactive amines, namely heterocyclic bases, as well as to carry out the reaction at milder conditions, especially at lower temperatures and for shorter periods of time, even with low reactive amines. Consequently, the yields are enhanced and the problems with inhibition of the reaction mixture are reduced. The polymerization itself has an advantage that, unlike the chloride anion, the sulfonate anion does not interfere the polymerization by transfer. The monomers prepared can be copolymerized with various known vinylic and divinylic comonomers, especially with those able to undergo a free-radical polymerization.

The invention permits to prepare, if needed, a broad choice of derivatives of numerous aliphatic or heterocyclic bases, both monomers and their polymers or copolymers. High-molecular-weight polymers or copolymers can be used, above all, as flocculants and coagulants in water treatment, where they gave very good results. The polymers and copolymers according to this invention can be further used in the way known for other cationic polyelectrolytes, for instance, as additives in paper production, for improving the dyeability of fibers, in production of selective permeable membranes, etc.

DESCRIPTION OF THE PREFERED EMBODIMENTS

The invention relates to quaternary salts, based upon methacrylic or acrylic esters, of the general formula II,

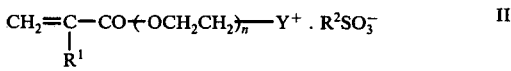

where
$R^1$ is H or $CH_3$
$R^2$ is $CH_3$, $C_6H_5$ or $p\text{-}CH_3C_6H_4$
$n$ is 1 or 2
and
$Y^+$ is

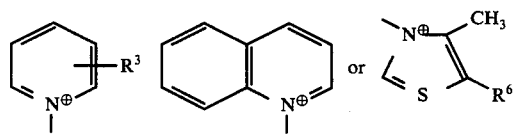

where
$R^3$ is H, $CH_3$, $CONH_2$, CHO, $COCH_3$ and
$R^4$ is H or $CH_2CH_2OH$.

The method for preparation of cationic quaternary salts, based upon methacrylic or acrylic esters, of the general formula II

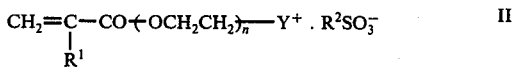

where
$R^1$ is H or $CH_3$ $R^2$ is $CH_3$, $C_6H_5$ or p-$CH_3C_6H_4$ n is 1 or 2 and $Y^+$ is either aliphatic, $-N^+(CH_3)_3$ or $-N^+(CH_3)_2CH_2CH_2OH$, or heterocyclic

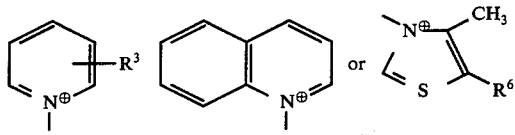

where $R^3$ is H, $CH_3$, $CONH_2$, CHO, $COCH_3$ and $R^4$ is H or $CH_2CH_2OH$, consists in the reaction of sulfoesters of the general formula III

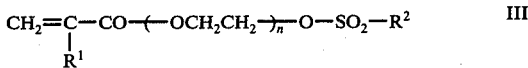

where $R^1$, $R^2$, and n have the same meaning as in the formula II, with the corresponding tertiary amine.

The reaction can be carried out in the presence of a polymerization inhibitor, without solvent or in an inert solvent, at the ambient or elevated temperature. The product can be purified, for example, by dissolving in water and subsequent extraction of unreacted components with a suitable solvent. The polymerization can be carried out in block, solution or emulsion in the presence of known free-radical initiators and also in the presence of further comonomers able to undergo the free-radical polymerization, e.g., methyl methacrylate, acrylonitrile, acrylamide, vinylpyridine, etc. Ion exchange resins are obtained when divinylic comonomers have been used, e.g., ethylene dimethacrylate, methylene-bis-acrylamide, etc. The aqueous solution of the monomer after extraction of an inhibitor may be directly used for the solution or emulsion polymerization, without isolation of the monomer.

An advantage of the invented method is employement of a large alkylation power of the sulfoester group. The reactions are carried out under mild conditions and reach high yields. It is also possible to prepare products derived from less reactive tertiary amines, which require in the preparation from chloro derivatives long reaction periods and high temperatures, i.e. the conditions when the thermally induced polymerization interferes even in the presence of an inhibitor. Another advantage is that sulfoester III can be prepared from a hydroxy derivative (e.g., 2-hydroxyethyl methacrylate), which contains various amounts of a divinylic component (ethylene dimethacrylate). The latter compound remains unchanged in the reaction mixture and is advantageously removed together with an inhibitor and other respective unreacted reaction components by extraction of the aqueous solution. This aqueous solution can be then advantageously directly used for polymerization.

The polymerization according to the invented method has the further advantage consisting in the fact that, unlike the chloride anion, the sulfonate anion does not interfere the polymerization by transfer.

This invention is further illustrated, but by no means limited, in the following examples.

EXAMPLE 1

Methacrylic ester of 2-hydroxyethyltrimethylammonium benzenesulfonate 2-(Benzenesulfonyloxy)ethyl methacrylate (20 parts) and 0.6 parts of nitrobenzene in 6.2 parts of trimethylamine and 45 parts of acetone was allowed to stand at 25° C for 16 hours and then heated to 40° C for 5 hours. Acetone and the excess of trimethylamine were removed in vacuum. The residue, crystalline in part, was dissolved in 125 parts of water and the solution was continuously extracted with ether for 2 hrs. The residual ether was removed from the aqueous phase in vacuum. The solution contained 19.7 parts of the monomer (80.9%) according to the titrimetric determination of anion (argentometric determination of chloride after exchange with an ion exchange resin).

EXAMPLE 2

Methacrylic ester of 2-(2-hydroxyethoxy)ethyltrimethylammonium benzenesulfonate

2-[2-(Benzenesulfonyloxy)ethoxy]ethyl methacrylate (12.6 parts), 0.2 parts of nitrobenzene and a solution of 3.5 parts of trimethylamine in 60 parts of acetone were allowed to stand at the ambient temperature for 40 hours. The reaction mixture was worked out similarly as in EXAMPLE 1, and the aqueous solution was obtained which contained 13.7 parts of the monomer (87% of theoretical yield).

EXAMPLE 3

Methacrylic ester of 1-(2-hydroxyethyl)pyridinium benzenesulfonate

A mixture of 50 parts of 2-(benzenesulfonyloxy)ethyl methacrylate, 16.1 parts of pyridine and 1 part of octylpyrocatechol was stirred and heated to 90° C for 105 min. The reaction product was dissolved in 250 parts of water and the solution was continuously extracted with ether for 2 hrs; the residues of ether were removed in vacuum. The resulting solution contained 60.6 parts of the monomer (94% of theoretical yield); determined as in EXAMPLE I.

EXAMPLE 4

Methacrylic ester of 1-(2-hydroxyethyl)pyridinium p-toluenesulfonate

A mixture of 20 parts of 2-(p-toluenesulfonyloxy)ethyl methacrylate, 6.1 parts of pyridine and 0.4 parts of octylpyrocatechol was stirred and heated to 90° C for 90 min. The reaction mixture was worked out analogously as in EXAMPLE 3 and the solution was obtained containing 24.5 parts of the monomer (95.6% of theoretical yield).

EXAMPLE 5

Methacrylic ester of 1-[2-(2-hydroxyethoxy)ethyl]pyridinium benzenesulfonate

A mixture of 20 parts of 2-[2-(benzenesulfonyloxy)ethoxy]ethyl methacrylate, 6.9 parts of pyridine and 0.5 parts of octylpyrocatechol was stirred and heated to 90° C for 105 min. The reaction mixture was worked out analogously as in EXAMPLE 3 and the solution was obtained containing 30.2 parts of the monomer (96.6% of theoretical yield).

EXAMPLE 6

Methacrylic ester of 1-[2-(2-hydroxyethoxy)ethyl]pyridinium p-toluenesulfonate

A mixture of 20 parts of 2-[2-(p-toluenesulfonyloxy)ethoxy]ethyl methacrylate, 5.3 parts of pyridine and 0.5 parts of octylpyrocatechol was stirred and heated to 90° C for 2 hrs. After the reaction mixture was worked out analogously as in EXAMPLE 3, the solution was obtained containing 24 parts of the monomer (97% of theoretical yield).

EXAMPLE 7

Methacrylic monoester of di(2-hydroxyethyl)dimethylammonium benzenesulfonate

A mixture of 20 parts of 2-(benzenesulfonyloxy)ethyl methacrylate, 6.58 parts of dimethylaminoethanol and 3 parts of nitrobenzene was heated to 90° C for 60 min. After the reaction mixture was worked out analogously as in EXAMPLE 3, the solution was obtained containing 25.4 parts of the monomer (95.4% of theoretical yield).

EXAMPLE 8

Methacrylic ester of 1-(2-hydroxyethyl)-3-carbamidopyridinium benzenesulfonate

A mixture of 12.2 parts of 2-(benzenesulfonyloxy)ethyl methacrylate, 5 parts of nicotinamide and 2.43 parts of nitrobenzene was stirred and heated to 90° C for 2 hrs. The reaction mixture gradually turned solid; the raw product melted 134° - 136° C and after crystallization from ethanol 137° - 138° C. The reaction mixture was worked out analogously as in EXAMPLE 3 and the solution was obtained containing 11 parts of the monomer (68.9% of theoretical yield).

EXAMPLE 9

Methacrylic ester of 1-[2-(2-hydroxyethoxy)ethyl]-3-carbamidopyridinium benzenesulfonate A mixture of 14.2 parts of 2-[2-(benzenesulfonyloxy)ethoxy]ethyl methacrylate, 5 parts of nicotinamide and 2.8 parts of nitrobenzene was stirred and heated to 90° C for 2 hours. The liquid product solidified by cooling into a crystalline mass melting 107° - 110° C; after recrystallization from ethanol the product melted at 116° C. The reaction mixture was worked out analogously as in EXAMPLE 3 and the solution was obtained containing 16.6 parts of the monomer (93.1% of theoretical yield).

EXAMPLE 10

Methacrylic ester of 3-[2-(2-hydroxyethoxy)ethyl]-4-methylthiazolium benzenesulfonate A mixture of 18 parts of 2-[2-(benzenesulfonyloxy)ethoxy]ethyl methacrylate, 5 parts of 4-methylthiazole and 3.6 parts of nitrobenzene was heated to 90° C for 150 min. The reaction mixture was worked out analogously as in EXAMPLE 3 and the solution was obtained containing 12.1 parts of the monomer (58.7% of theoretical yield).

EXAMPLE 11

Methacrylic ester of 3-[2-(2-hydroxyethoxy)ethyl]-4-methyl-5-(2-hydroxyethyl)thiazolium benzenesulfonate A mixture of 7.28 parts of 2-[2-(benzenesulfonyloxy)ethoxy]ethyl methacrylate, 3 parts of 4-methyl-5-(2-hydroxyethyl)thiazole and 1.1 parts of nitrobenzene was heated to 90° C for 150 min. The reaction mixture was worked out analogously as in EXAMPLE 3 and the solution was obtained containing 6.33 parts of the monomer (59.7%).

EXAMPLE 12

Methacrylic ester of 2-hydroxyethyltrimethylammonium toluenesulfonate 2-(Toluenesulfonyloxy)ethyl methacrylate (50 parts) and 0.85 parts of nitrobenzene in a solution of 14.2 parts of trimethylamine and 90 parts of acetone were allowed to stand at 25° C for 15 hrs and then heated to 40° C for 5 hrs. The product was freed from acetone and excessive trimethylamine in vacuum. A crystalline residue (m.p. 124° - 5° C; from acetone) was dissolved in 125 parts of water and continuously extracted by ether for 2 hrs. The aqueous solution was freed from ether residues in vacuum and contained 42.3 parts of the monomer, according to a titrimetric determination of the anion.

EXAMPLE 13

Acrylic ester of 2-hydroxyethyltrimethylammonium benzenesulfonate 2-(Benzenesulfonyloxy)ethyl acrylate (10 parts) and 0.32 parts of nitrobenzene in a solution of 3.2 parts of trimethylamine and 21 parts of tetrahydrofuran were allowed to stand at 25° C for 18 hrs. The product gradually precipitated from the solution. The excessive trimethylamine and tetrahydrofuran were evaporated in vacuum. The crystalline residue was dissolved in 68 parts of water and continuously extracted with ether for 2 hrs. The resulting aqueous solution contained 9.75 parts of the monomer, according to a titrimetric determination.

EXAMPLE 14

Polymerization of methacrylic ester of 1-(2-hydroxy)ethylpyridinium benzenesulfonate A solution of 25.8 parts of the monomer in 100 parts of water was stirred and heated to 60° C in an inert atmosphere with 0.036 parts of azo-bis(methyl isobutyrate) for 4 hrs. The polymer can be isolated by precipitation into excess of acetone. Conversion of the monomer 90%, $[\eta] = 1.32$ (in 0.5 N KCl).

EXAMPLE 15

Polymerization of methacrylic ester of 1-[2-(2-hydroxyethoxy)ethyl]pyridinium benzenesulfonate A solution of 24.2 parts of the monomer in 85 parts of water was stirred and heated to 60° C in an inert atmosphere with 0.015 parts of azo-bis(methylisobutyrate) for 6 hrs. By precipitation into acetone 21.3 parts of the polymer was obtained, $[\eta] = 2.5$ (in 0.5 N KCl).

EXAMPLE 16

Polymerization of methacrylic ester of 1-(2-hydroxyethyl)pyridinium p-toluenesulfonate A solution of 10 parts of the monomer in 36 parts of water was heated to 60° C with 0.027 parts of azo-bis(-methyl isobutyrate) under an inert atmosphere for 6 hrs. After cooling the solution down to the ambient temperature, 9 parts of the polymer precipitated, $[\eta] = 0.61$ (in 0.5 N KCl).

EXAMPLE 17

Polymerization of methacrylic ester of 3-[2-(2-hydroxyethoxy)ethyl]-4-methylthiazolium benzenesulfonate A solution of 5 parts of the monomer in 27 parts of water was heated to 50° C under an inert atmosphere with 0.006 parts of azo-bis(methyl isobutyrate) for 10 hours. By precipitation into acetone 4.41 parts of the polymer was obtained, $[\eta] = 1.58$ (in 0.5 N KCl).

EXAMPLE 18

Polymerization of methacrylic ester of 2-(2-hydroxyethoxy)ethyltrimethylammonium benzenesulfonate A solution of 6.85 parts of the monomer in 40 parts of water was heated to 60° C under an inert atmosphere with 0.025 parts of potassium persulfate for 4 hrs. The viscous solution was precipitated into an excess of acetone and 5.60 parts of the polymer was obtained, $[\eta] = 1.05$ (in 0.5 N KCl).

EXAMPLE 19

Copolymerization of methyl methacrylate in emulsion

A mixture of 25 parts of methyl methacrylate, 4.27 parts of methacrylic ester of 1-(2-hydroxyethyl)-pyridinium benzenesulfonate, 25 parts of water and 0.05 parts of potassium persulfate was agitated and heated to 60° C under an inert atmosphere for 6 hrs. The thick reaction mixture was stirred with 50 parts of water, centrifugated and the residue was washed three times with 50 parts of water and dried; 22.5 parts of the copolymer was obtained which contained 0.35% N.

EXAMPLE 20

Polymerization of methacrylic ester of 2-hydroxyethytrimethylammonium benzenesulfonate A solution of 10 parts of the monomer in 51 parts of water was heated to 60° C under an inert atmosphere with 0.035 parts of azo-bis(methyl isobutyrate) for 8 hrs. The polymer (8.7 parts) was obtained by precipitation into 450 parts of acetone; $[\eta] = 1.6$ (in 0.5 N KCl).

EXAMPLE 21

Polymerization of methacrylic ester of 3-(2-hydroxyethyl)-4-methylthiazolium benzenesulfonate A solution of 5 parts of the monomer in 21.4 parts of water was heated to 60° C with 0.011 parts of azo-bis(-methyl isobutyrate) under an inert atmosphere for 6 hrs. The polymer (4.45 parts) was obtained by precipitation into 200 parts of acetone; $[\eta] = 0.86$ (in 0.5 N KCl).

EXAMPLE 22

Polymerization of methacrylic ester of 1-(2-hydroxyethyl)-3-carbamidopyridinium benzenesulfonate A solution of 6 parts of the monomer in 40 parts of water and 0.012 parts of azo-bis(methyl isobutyrate) was heated to 60° C in an inert atmosphere for 20 hrs. The polymer (2.54 parts) was obtained by precipitation into 320 parts of acetone.

EXAMPLE 23

Polymerization of acrylic ester of 2-hydroxyethyltrimethylammonium benzenesulfonate A solution of 5 parts of the monomer in 10.7 parts of water and 0.017 parts of azo-bis(methyl isobutyrate) was heated to 55° C under an inert atmosphere for 6 hrs. The polymer (4.0 parts) was obtained by precipitation into 124 parts of acetone; $[\eta] = 0.36$ (in 0.5 N KCl).

EXAMPLE 24

Polymerization of methacrylic ester of 2-hydroxyethyltrimethylammonium p-toluenesulfonate A solution of 5 parts of the monomer in 26.2 parts of water and 0.01 part of azo-bis(methyl isobutyrate) was heated to 60° C for 3 hrs. The polymer (4.4 parts was obtained by precipitation into 242 parts of acetone; $[\eta] = 1.18$ (in 0.5 N KCl).

EXAMPLE 25

Copolymerization of methacrylic ester of 2-(hydroxyethyl)trimethylammonium p-toluenesulfonate with acrylamide A solution of 2.68 parts of methacrylic ester of 2-(hydroxyethyl)-trimethylammonium toluenesulfonate and 5.0 parts of acrylamide 32.7 parts of water with 0.027 parts of $(NH_4)_2S_2O_8$ and 0.021 parts of $Na_2S_2O_4$ was heated to 45° C under an inert atmosphere for 3 hrs. The polymer (7.5 parts) containing 3.16% S was obtained by precipitation into 310 parts of acetone; $[\eta] = 1.12$ (in 0.5 N KCl).

We claim:

1. Cationic quaternary salts based upon methacrylic or acrylic esters and having the general formula II $$CH_2=C-CO+OCH_2CH_2)_n-Y^+ \cdot R^2SO_3^- \qquad II$$
$$\phantom{CH_2=}|$$
$$\phantom{CH_2=}R^1$$

where
$R^1$ is H or $CH_3$
$R^2$ is $CH_3$, $C_6H_5$ or p-$CH_3C_6H_4$
$n$ is 1 or 2
and
$Y^+$ is

[structures: pyridinium with $R^3$ substituent; quinolinium; or thiazolium with $R^6$ and $CH_3$]

where
$R^3$ is H, $CH_3$, $CONH_2$, CHO, $COCH_3$
and $R^4$ is H or $CH_2CH_2OH$.

2. A quaternary salt according to claim 1, wherein $R^1$ is $CH_3$, $R^2$ is $C_6H_5$, n is 1 or 2, and $Y^+$ is

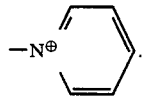

3. A quaternary salt according to claim 1, wherein $R^1$ is $CH_3$, $R^2$ is p-$CH_3C_6H_4$, n is 1 or 2, and $Y^+$ is

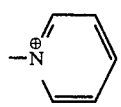

4. A quaternary salt according to claim 1, wherein $R^1$ is $CH_3$, $R^2$ is $C_6H_5$, n is 1, or 2 and $Y^+$ is

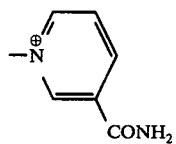

5. A quaternary salt according to claim 1, wherein $R^1$ is $CH_3$, $R^2$ is $C_6H_5$, n is 2, and $Y^+$ is

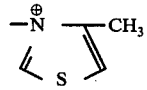

6. A quaternary salt according to claim 1, wherein $R^1$ is $CH_3$, $R^2$ is $C_6H_5$, n is 2, and $Y^+$ is

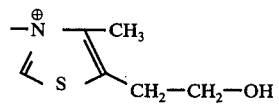

* * * * *